US00PP21417P2

(12) United States Plant Patent
Roethling

(10) Patent No.: US PP21,417 P2
(45) Date of Patent: Oct. 26, 2010

(54) INDIAN HAWTHORN PLANT NAMED 'FIESTA'

(50) Latin Name: *Rhaphiolepis indica*
Varietal Denomination: Fiesta

(76) Inventor: Jon L. Roethling, 5725 Gumtree Rd., Winston Salem, NC (US) 27107

( * ) Notice: Subject to any disclaimer, the term of this patent is extended or adjusted under 35 U.S.C. 154(b) by 0 days.

(21) Appl. No.: 12/387,844

(22) Filed: May 7, 2009

Related U.S. Application Data

(60) Provisional application No. 61/127,230, filed on May 12, 2008.

(51) Int. Cl.
*A01H 5/00* (2006.01)

(52) U.S. Cl. ..... Plt./254

(58) Field of Classification Search ..... Plt./254
See application file for complete search history.

*Primary Examiner*—Kent L Bell

(57) ABSTRACT

A new cultivar of *Rhaphiolepis* named 'FIESTA' that is characterized by evergreen foliage which is marginally variegated cream-white and green, and whose flowers are light pink in bud, opening to white. In combination, these characteristics distinguish 'FIESTA' from all other varieties of *Rhaphiolepis* known to the inventor.

2 Drawing Sheets

Genus: *Rhaphiolepis.*
Species: *indica.*
Denomination: 'FIESTA'.

BACKGROUND OF THE INVENTION

The present invention relates to a new and distinct cultivar of Indian Hawthorn, or *Rhaphiolepis* plant which is grown as an ornamental evergreen shrub for use in the garden and landscape. The new cultivar is known botanically as *Rhaphiolepis indica* and will be referred to hereinafter by the cultivar name 'FIESTA'.

'FIESTA' was discovered by the inventor in a cultivated private garden in Waxhaw, N.C. in 2002. The inventor discovered 'FIESTA' as a naturally occurring variegated branch sport which was growing on a single non-variegated plant of *Rhaphiolepis indica*. It is not known whether this single plant is a named cultivar of *Rhaphiolepis*, or whether it had been grown from seed. In 2002, the inventor excised the variegated branch and made semi-hardwood cuttings in order to establish the new variety on its own roots. By 2003, the inventor had determined that the variegated characteristics were being maintained on the newly established plants. Since that time, following further successive cycles of asexual reproduction using semi- hardwood cuttings, the inventor has concluded that 'FIESTA' is stable and reproduces true to type.

There are no cultivars of variegated Indian HAWTHORN known to the inventor, and the closest comparison plants are all non-variegated. Thus 'FIESTA' is clearly distinguishable from its parent and from all cultivars of *Rhaphiolepis* Known to the Inventor by virtue of its pronounced and distinctive cream-white variegated foliage.

SUMMARY OF THE INVENTION

The distinguishing characteristics of 'FIESTA' are as follows: In combination these traits set 'FIESTA' apart from all other existing varieties of *Rhaphiolepis indica* known to the inventor. 'FIESTA' has not been tested under all possible conditions and phenotypic differences may be observed with variations in environmental, climatic, and cultural conditions.

1. 'FIESTA' is evergreen.
2. The foliage of 'FIESTA' is marginally variegated cream-white and green.
3. Each leaf of 'FIESTA' exhibits a broad cream-white margin, including the apex.
4. Each leaf of 'FIESTA' exhibits a central patch of mid green which does not extend to any margin.
5. The flowers of 'FIESTA' are light pink in bud opening to white in color.
6. 'FIESTA' blooms from early to mid-spring.
7. A two year old plant of 'FIESTA' is approximately 35cm in height and 75 cm in width.
8. 'FIESTA' is hardy to USDA Zone 7.
9. 'FIESTA' requires sun to partial shade.

BRIEF DESCRIPTION OF THE DRAWINGS

The accompanying color drawings illustrate the overall appearance of 'FIESTA' showing the colors of its foliage and flowers as true as it is reasonably possible to obtain in colored reproductions of this type.

The drawing labeled as FIG. 1 depicts a single plant of 'FIESTA' in foliage in May. The illustrated plant is three years old and has been planted in a 2 gallon container and grown out of doors in Raleigh, N.C.

Figure 1:
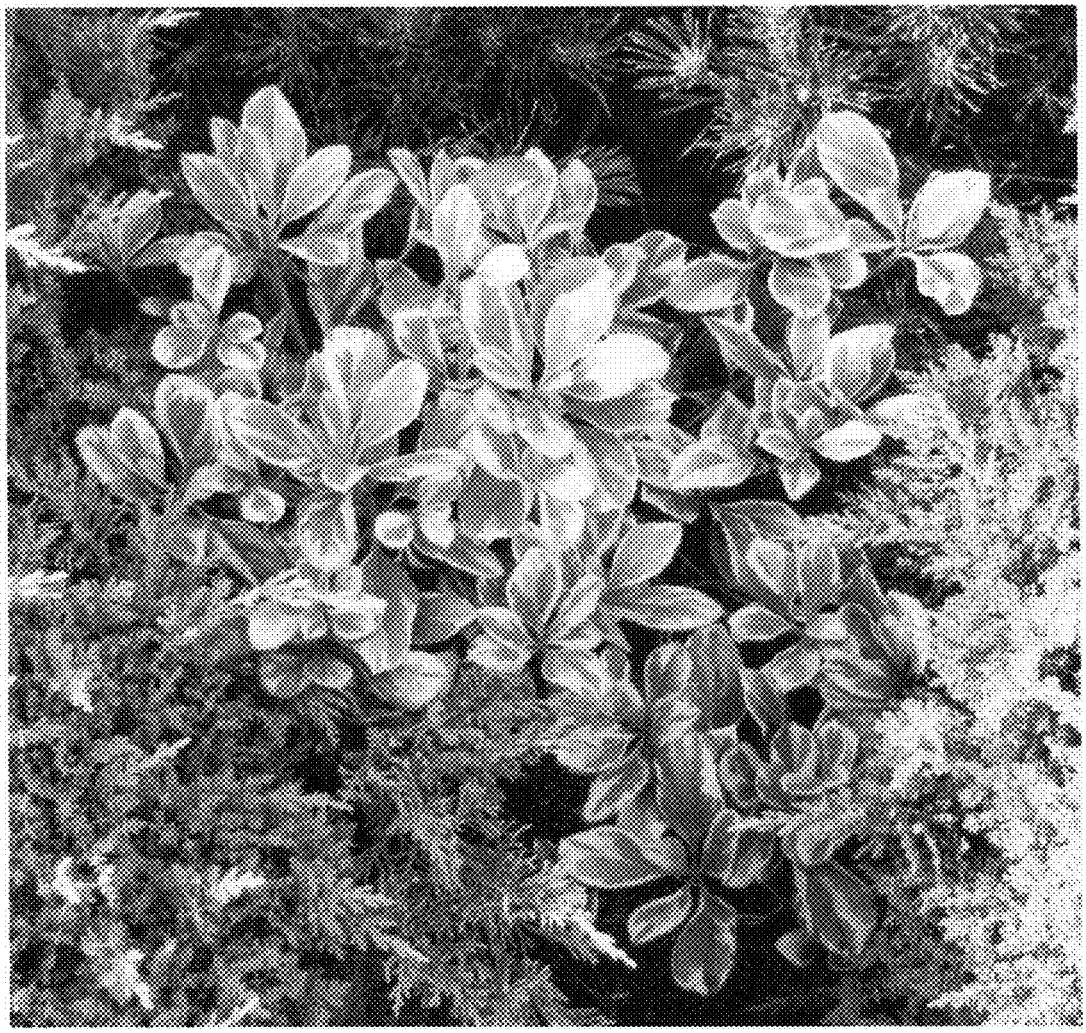
Figure 2:
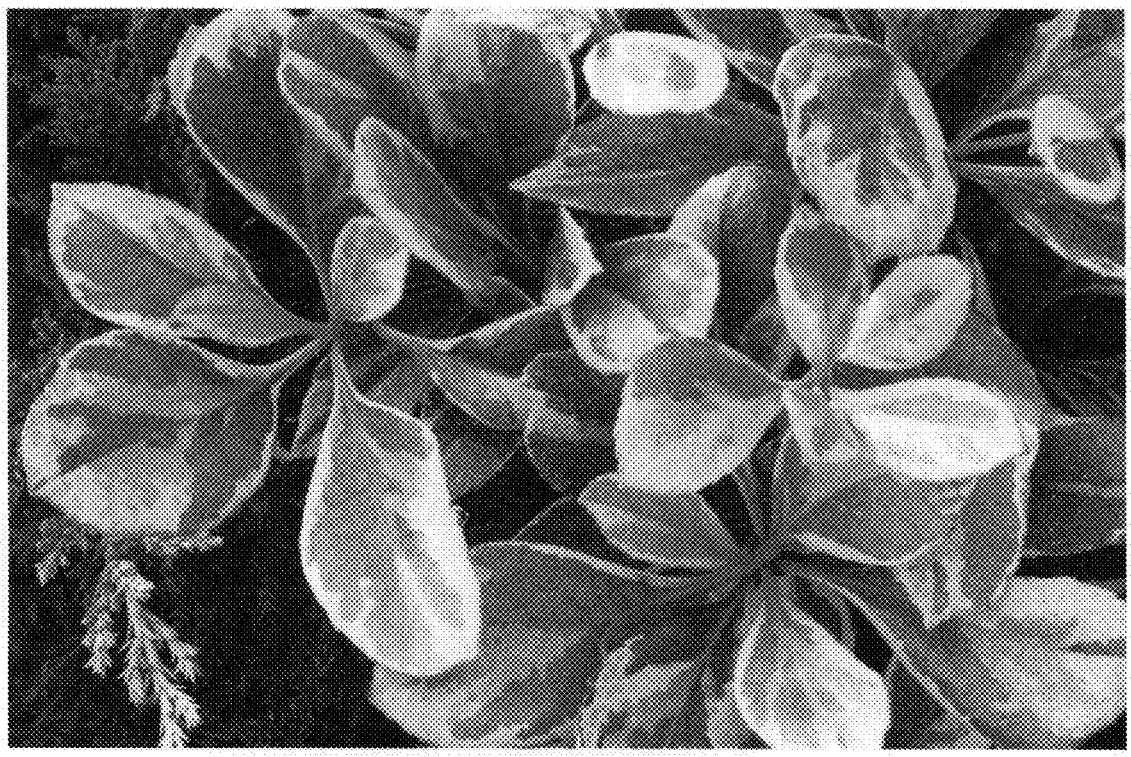

The drawing labeled as FIG. 2 depicts a close-up view of the foliage of 'FIESTA'. Both drawings were made using conventional techniques and although the colors of and within the variegated foliage may appear different from actual color due to light reflectance, their color is as accurate as possible by conventional photography.

DETAILED BOTANICAL DESCRIPTION OF THE PLANT

The following is a detailed botanical description of 'FIESTA'. Unless otherwise stated herein, observations, measurements, values and comparisons were compiled from a two year old plant grown out of doors in Colfax, N.C. Color determinations are made in accordance with The 2001 Royal Horticultural Society Colour Chart from London, England, except where general color terms of ordinary dictionary significance are used. Growing conditions are similar to the species.

Botanical classification:

*Genus.*—*Rhaphiolepis.*

*Species.*—*indica.*

*Cultivar name.*—'Fiesta'.

Propagation and growing information:

*Means of propagation.*—Semi-hardwood stem cuttings.

*Rooting habit.*—Dense and highly branched, fibrous root system.

*Time to develop roots.*—3 to 4 weeks.

*Crop time to a finished container.*—1 year to 2 years.

*Typical size of finished saleable container.*—1 gallon container to 3 gallon container.

*Plant habit.*—Mounding broadleaf evergreen shrub.

*Use of plant.*—Landscape evergreen shrub.

*Growth rate.*—Approximately 30 cm per year per branch, or faster in ideal conditions.

*Height of plant.*—35 cm at 2 years.

*Width of plant.*—75 cm at 2 years.

*Hardiness.*—USDA Cold Hardiness zone 7b (0 to 5 degrees F.).

*Flowering season.*—Spring.

Branching:

*Branching habit.*—Sympodial.

Stem:

*Stem color.*—199B.

*Stem shape.*—Terete.

*Stem width.*—3 to 4 mm.

*Stem surface.*—Glabrous.

*Pubescence.*—mostly absent; occasional very short pilose hairs.

*Stem length* (*main stems*).—75 to 160 mm.

*Stem length* (*secondary stems*).—40 to 70 mm.

*Internode length.*—12 to 25 mm.

*Twig color*—146C.

*Twig shape.*—Terete.

*Twig width.*—2 to 3 mm.

*Twig surface.*—Pubescent.

*Twig pubescence.*—Hairs densely packed, long floccose, tawny-white in color.

Foliage:

*Leaf arrangement.*—Alternate to subopposite, occasionally in pseudo-whorls.

*Leaf division.*—Simple.

*Leaf shape.*—Elliptic to oblanceolate, sometimes ovate.

*Leaf length* (*blade only*).—30 to 60 mm.

*Leaf width.*—12 to 35 mm.

*Leaf tip.*—Acute to submucronate.

*Leaf base.*—Cuneate to attenuate.

*Quantity of leaves per stem.*—6 to 8.

*Leaf venation pattern.*—Reticulate.

*Vein color* (*adaxial surface*).—191B.

*Vein color* (*abaxial surface*).—153A.

*Margin type.*—Serrate, sometimes sparsely so.

*Leaf surface* (*adaxial*).—Glabrous, waxy, with few floccose hairs on midrib.

*Leaf surface* (*abaxial*).—Glabrous, with short pilose hairs on midrib and secondary veins.

*Leaf color in spring, fully mature leaves* (*adaxial*).—Mottled 138A, 138B, 139A, 139B, 191B, 191A are all individually present; variegation colored 158A.

*Leaf color in spring, fully mature leaves* (*abaxial*).—138B.

*Leaf color in spring, newly flushing leaves* (*adaxial*).—As fully mature, as above, except with 163A colored overlay, this color contributed by presence of densely packed, but caducous, tomentose hairs.

*Leaf color in spring, newly flushing leaves* (*abaxial*).—As adaxial above.

*Leaf color in winter* (*adaxial*).—As fully mature leaves in spring as above, except strongly tinged 63A to 59C.

*Leaf color in winter* (*abaxial*).—As fully mature leaves in spring.

*Leaf attachment.*—Petiolate.

*Petiole length.*—5 to 20 mm.

*Petiole diameter.*—2 to 3 mm.

*Petiole color.*—138B.

*Petiole surface.*—Pubescent (young leaves) to subglabrous (mature leaves).

*Pubescence* (*where present*).—Short pilose hairs.

Foliage variegation:

*Location on leaf.*—Marginal.

*Description of variegation.*—Variegation typically comprises ⅛ to ¼ of leaf, although in some leaves up to ½ of the blade is variegated; streaks of variegation are unevenly overlaid on leaves, creating a mottled look; some leaves bear variegated sectors extending away from the margin nearly to the midrib, but most leaves do not have these sectors.

Inflorescence:

*Inflorescence form.*—Paniculate.

*Flower arrangement.*—Terminal.

*Quantity of flowers per inflorescence.*—9 to 20.

*Quantity of inflorescences per plant.*—50 or more when plant is 2 years of age.

*Time and duration of flowering.*—3 to 4 weeks.

Bracts:

*Persistence.*—Caduceus.

*Bract length.*—4 to 8 mm.

*Bract width.*—1 mm or less.

*Bract color.*—153B, tinged apically 59A.

*Bract shape.*—Linear.

Flower:

*Pedicels and peduncles.*—Pedicel length: 5 to 10 mm. Pedicel width: 1 to 2 mm. Peduncle length: 50 to 60 mm. Peduncle width: 1 to 2 mm. Pedicel and peduncle shape: terete. Pedicel and peduncle color: 146C. Pedicel and peduncle surface: tomentose, hairs tawny.

*Flower bud.*—Bud shape: elliptoid. Bud color: enclosed by sepals colors, 146C in color. Bud surface: see Calyx surface below. Bud diameter: 5 mm. Bud length: 3 mm.

*Open Flowers.*—Diameter of flower (including calyx, corolla, petals): 25 to 30 mm. Height or depth of flower (base of hypanthium to anthers): 10 mm.

*Calyx.*—Calyx lobe shape: acuminate. Calyx lobe length: 3 to 5 mm. Calyx lobe width: less than 1 mm. Calyx color (outer surface): 146C , tinged 59A apically. Calyx color (inner surface): 146C. Calyx surface (outer and inner surfaces): pubescent, pilose-tomentose; ciliate on margins; hairs tawny-brown in color except at apex of hypanthium where are colored 59A.

*Sepals.*—Sepals: Present, fused into a single calyx; calyx fused with the staminal filaments into a Hypanthium. Number of sepals: 5 calyx lobes (not separated into sepals). Sepals fused or unfused: fused.

*Petals.*—Petals fused or unfused: unfused. Petal shape: oblanceolate, concave adaxially. Petal length: 14 to 20 mm. Petal width: 5 to 8 mm. Petal limbs: short, comprising 3 to 4 mm of overall petal length. Number of petals: 5. Petal color (adaxial surface): white. Petal color (abaxial surface): 63B, fading to 62D, in bud, white afterward upon floral unfolding. Petal surface (adaxial surface): glabrous, ciliate on margins. Petal surface (abaxial surface): glabrous.

*Reproductive organs.*—Number of stamens: 10 to 15. Fused or unfused at base: fused together (along with calyx) into a hypanthium. Filaments: Filament length: 6 to 7 mm. Filament width: less than 1 mm. Filament color (filament): white, changing to 61A, 61B after 24 to 48 hours; onset of coloration concurrent with anther drying and end of pollen release. Anthers: Anther shape: elliptic. Anther length: 1 mm. Anther width: less than 1 mm. Anther color: yellow, turning brown at senescence. Pollen: Pollen color: yellow. Pollen amount: little. Gynoecium: Position: set down in hypanthial cup. Stigma: Stigma shape: round. Stigma length: less than 1 mm. Stigma width: less than 1 mm. Stigma color: yellow, turning brown at senescence. Styles: 2, fused at base, forking midway toward apex, revealing 2 separate stigmatic surfaces. Style shape: linear. Style length: 6 to 7 mm. Style width: less than 1 mm. Style color: white, aging to 61A, 61B. Ovary: Ovary position: inferior, perigynous. Ovary shape: elliptoid. Ovary length: 1 to 2 mm. Ovary width: less than 1 mm. Ovary color: 191A.

*Seed.*—Seed has not been observed.

The invention claimed is:

1. A new and distinct cultivar of *Rhaphiolepis* plant named 'FIESTA' as described and illustrated herein.

* * * * *